US 6,738,660 B2

(12) United States Patent
Hakomori et al.

(10) Patent No.: US 6,738,660 B2
(45) Date of Patent: May 18, 2004

(54) RESINOUS COVER FOR USE IN BIOELECTRICAL IMPEDANCE MEASURING APPARATUS

(75) Inventors: Ikuo Hakomori, Sakado (JP); Yoshikazu Yoshida, Tokyo (JP)

(73) Assignee: Tanita Corporation, Tokyo (JP)

( * ) Notice: Subject to any disclaimer, the term of this patent is extended or adjusted under 35 U.S.C. 154(b) by 45 days.

(21) Appl. No.: 09/989,203

(22) Filed: Nov. 21, 2001

(65) Prior Publication Data

US 2002/0072687 A1 Jun. 13, 2002

(30) Foreign Application Priority Data

Dec. 8, 2000 (JP) ........................................ 2000-374118

(51) Int. Cl.⁷ ................................................. A61B 5/05
(52) U.S. Cl. ...................................................... 600/547
(58) Field of Search ................................. 600/547, 506, 600/587; 382/115; 340/5.52, 5.82

(56) References Cited

U.S. PATENT DOCUMENTS 5,125,405 A    6/1992    Schmid 6,292,690 B1 *  9/2001   Petrucelli et al. ........... 600/547
6,507,662 B1 *  1/2003   Brooks ....................... 600/506
6,532,384 B1 *  3/2003   Fukuda ....................... 600/547

FOREIGN PATENT DOCUMENTS

WO        WO 90/09758          9/1990

* cited by examiner

*Primary Examiner*—Max F. Hindenburg
*Assistant Examiner*—Brian Szmal
(74) *Attorney, Agent, or Firm*—McDermott, Will & Emery

(57) ABSTRACT

A resinous cover for use in a bioelectrical impedance measuring apparatus is provided, in which the processes for manufacturing the resinous cover are significantly decreased in number and the components thereof are decreased in number and therefore the cost thereof is reduced to a low level. Further, such a resinous cover cause little the soles of feet to feel cool when the bioelectrical impedance is being measured, and the area of the electrode which comes into contact with the soles of feet is wide. A resinous cover for use in a bioelectrical impedance measuring apparatus, comprising electrodes and an insulating portion provided among the electrodes, wherein the electrodes and the insulating portion are integrally-molded.

17 Claims, 6 Drawing Sheets

RESINOUS COVER FOR USE IN BIOELECTRICAL IMPEDANCE MEASURING APPARATUS

BACKGROUND OF THE INVENTION

1. Field of the Invention

The present invention relates to a resinous cover for use in a bioelectrical impedance measuring apparatus for measuring bioelectrical impedance to calculate a percent fat, a total body water or the like based on said measured bioelectrical impedance.

2. Prior Art

Conventionally, a body fat meter with body weight meter for measuring bioelectrical impedance in an organism by using a pair of current supplying electrodes and a pair of voltage measuring electrodes so as to calculate the percent fat or the like (hereinafter referred to as "body fat meter"), has been proposed. As shown in a plane view of the body fat meter in FIG. 6 and a sectional side view taken along line C—C of FIG. 7, a resinous cover 40 equipped with said electrodes comprises electrode attachment portions 41, four metal electrodes 42, double-sided tapes 43 for attaching the electrodes 42 to the attachment portions 41, lead wires 45, and an operational display unit 13 for inputting personal data, such as a height, or for displaying the resulting measurements. The operational display unit 13 comprises a display part 13a for displaying a weight, a percent fat, etc.; a set button 13b for setting an age, a sex, a height, etc.; and a selection button 13c.

Referring now to a flow chart in FIG. 8, processes for manufacturing the resinous cover 40 will be explained. In step S11, the metal electrodes 42 are molded. In step S12, the resinous cover 40 is molded. In step S13, one end of each of the respective lead wires 45 is soldered to each of the electrodes 42, respectively. In step S14, the double-sided tapes 43 are stuck on the back sides of the electrodes 42, respectively. In step S15, the other ends 45a of the respective lead wires 45 are respectively drawn through openings 44 to the backside of the resinous cover 40. In step S16, the electrodes 42 are respectively embedded in the attachment portions 41 provided in the resinous cover 40. In step S17, the operational display unit 13 is embedded in the resinous cover 40. In step S18, the resinous cover 40 is embedded in a cover 46. In step S19, the other ends 45a of the respective lead wires 45 are respectively wired to a body fat meter control unit which is not shown in the figures.

As described above, conventionally, since the electrodes 42 of the body fat meter are molded independently and then manually attached to the resinous cover 40, the manufacturing processes are increased in number and components are increased in number, and therefore the cost of the assembly and the components become high. Also, since the materials of the electrodes are metal, when measuring the bioelectrical impedance, these electrodes cause the soles of feet to feel disagreeably cool. In addition, because of the designs and so forth, it becomes difficult to reserve a sufficient area of the electrodes for coming into contact with the soles of feet.

SUMMARY OF THE INVENTION

The object of the present invention is to provide a resinous cover for use in a bioelectrical impedance measuring apparatus, in which, to solve the above problems in the prior art, the manufacturing processes are decreased in number and components are decreased in number and therefore the cost is reduced to a low level; apparent shape of the electrode is allowed to be freely designed; and further such a resinous cover prevents the soles of feet from feeling very disagreeably cool and the area of the electrodes for coming into contact with the soles of feet is sufficient.

The feature of the resinous cover for use in the bioelectrical impedance measuring apparatus according to the present invention resides in integrally-molding the electrodes and an insulating portion.

According to an aspect of the present invention, the material of said electrodes is conductive resin.

According to another aspect of the present invention, the integrally-molding method is multicolored molding.

According to further aspect of the present invention, the degree of smoothness of the surfaces of said electrodes is different from that of said insulating portion.

According to yet further aspect of the present invention, the surface of either of said electrodes or said insulating portion is made rough and the surface of the other is made smooth.

According to yet further aspect of the present invention, the color of said electrodes and that of said insulating portion are different from each other.

According to yet further aspect of the present invention, apparent electrodes are formed within the areas occupied by said electrodes.

According to yet further aspect of the present invention, each of the areas of said electrodes is more than two times that of its apparent electrode.

According to yet further aspect of the present invention, the color of the areas occupied by said electrodes other than the areas occupied by said apparent electrodes and the color of said insulating portion are the same as each other.

BRIEF DESCRIPTION OF THE DRAWINGS

The object and features of the present invention will become more apparent from the consideration of the following detailed description taken in conjunction with the accompanying drawings in which.

DESCRIPTION OF PREFERRED EMBODIMENTS

With reference to the drawings, the embodiments of the present invention will now be explained.

Figure 1:
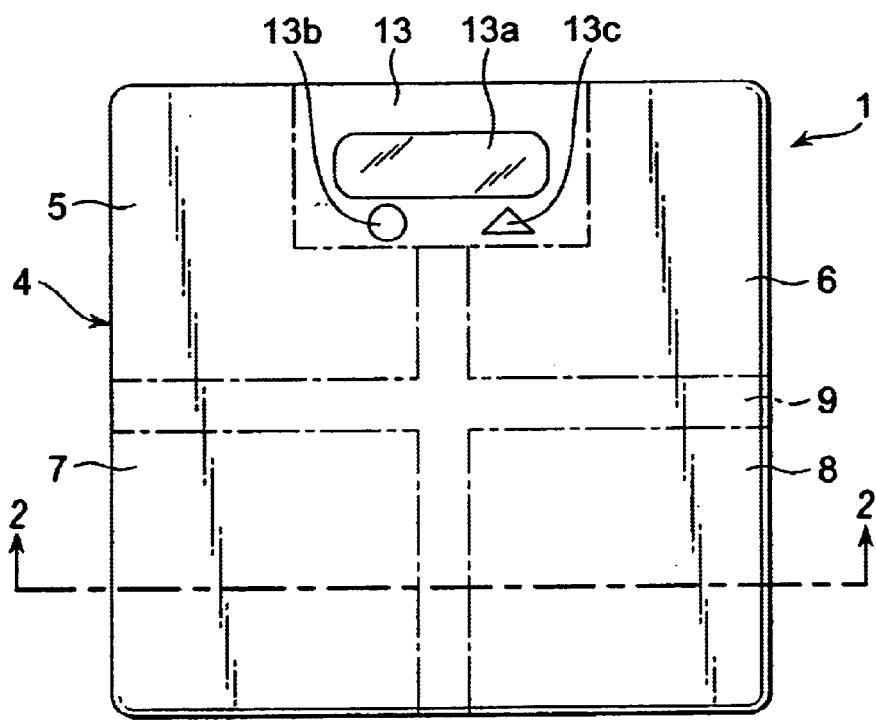
FIG. 1 is a top view of a body fat meter according to the present invention.
Figure 2:
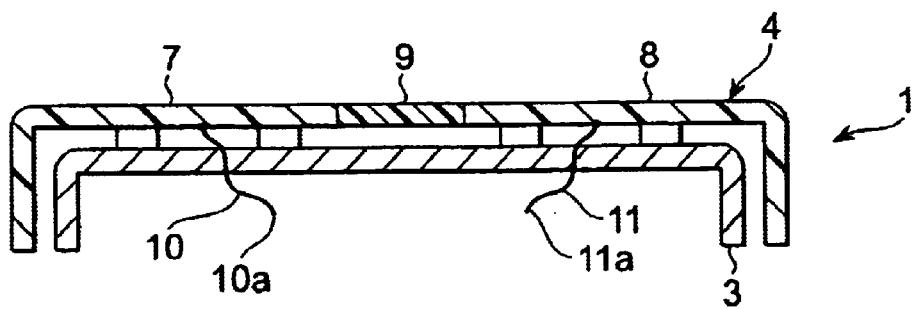
FIG. 2 is a sectional side view taken along line A—A of FIG. 1 according to the present invention.

FIG. 1 and FIG. 2 illustrates a top view of a resinous cover of a body fat meter 1 according to the present invention and a sectional side view taken along line A—A of FIG. 1, respectively. "3" indicates a metal cover. In the cover 3, a body fat meter control unit which is not shown in the figures, is internally installed.

Figure 6:
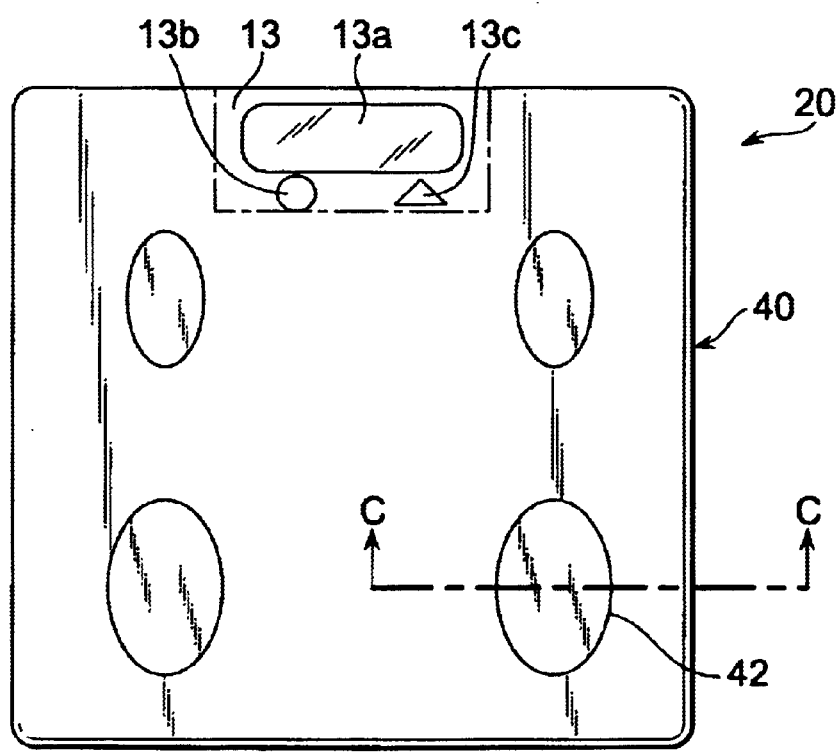
FIG. 6 is a top view of a conventional body fat meter.
Figure 7:
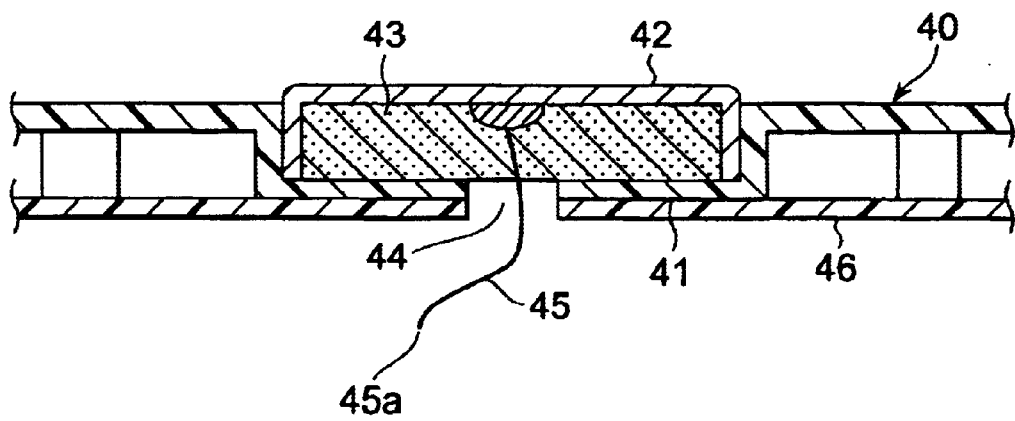
FIG. 7 is a sectional side view taken along lines C—C of FIG. 6.

A resinous cover 4 comprises a pair of current supplying electrodes 5, 6 made from conductive resin; voltage measuring electrodes 7, 8; an insulating portion 9; lead wires 10, 11; and an operational display unit 13. The operational display unit 13 comprises a display part 13a for displaying a weight, a percent fat, etc.; a set button 13b for setting an age, a sex, a height, etc.; and a selection button 13c. The parts in FIGS. 1 and 2 similar to those in FIG. 6 are indicated by the same references numbers as those in FIG. 6.

Figure 3:
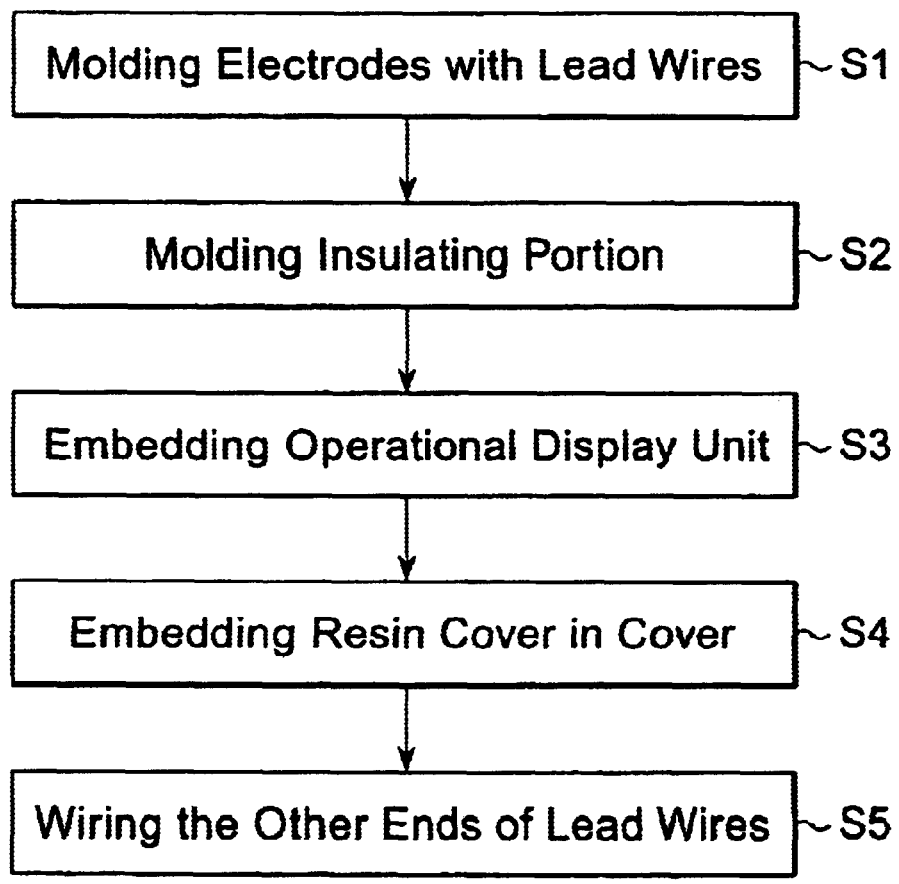
FIG. 3 is a flow chart showing manufacturing processes according to the present invention.

With reference to a flow chart in FIG. 3, processes for manufacturing the resinous cover according to the present invention will now be explained.

In step S1, electrodes 5 to 8 are molded from conductive resin by a multicolored molding machine. At this time, electrodes are molded such that one end of each of the lead wires is embedded in the electrodes, respectively. In step S2, the insulating portion 9 is molded from resin by the multicolored molding machine. In steps S1 and S2, a resinous cover 4 is integrally-molded by a multicolored molding technique. In step S3, the operational display unit 13 is embedded in the resinous cover 4. In step S4, the resinous cover 4 is mounted over the cover 3. In step S5, the other ends 10a, 11a of the respective lead wires 10, 11 are respectively connected to the body fat meter control unit, which is not shown.

Figure 8:
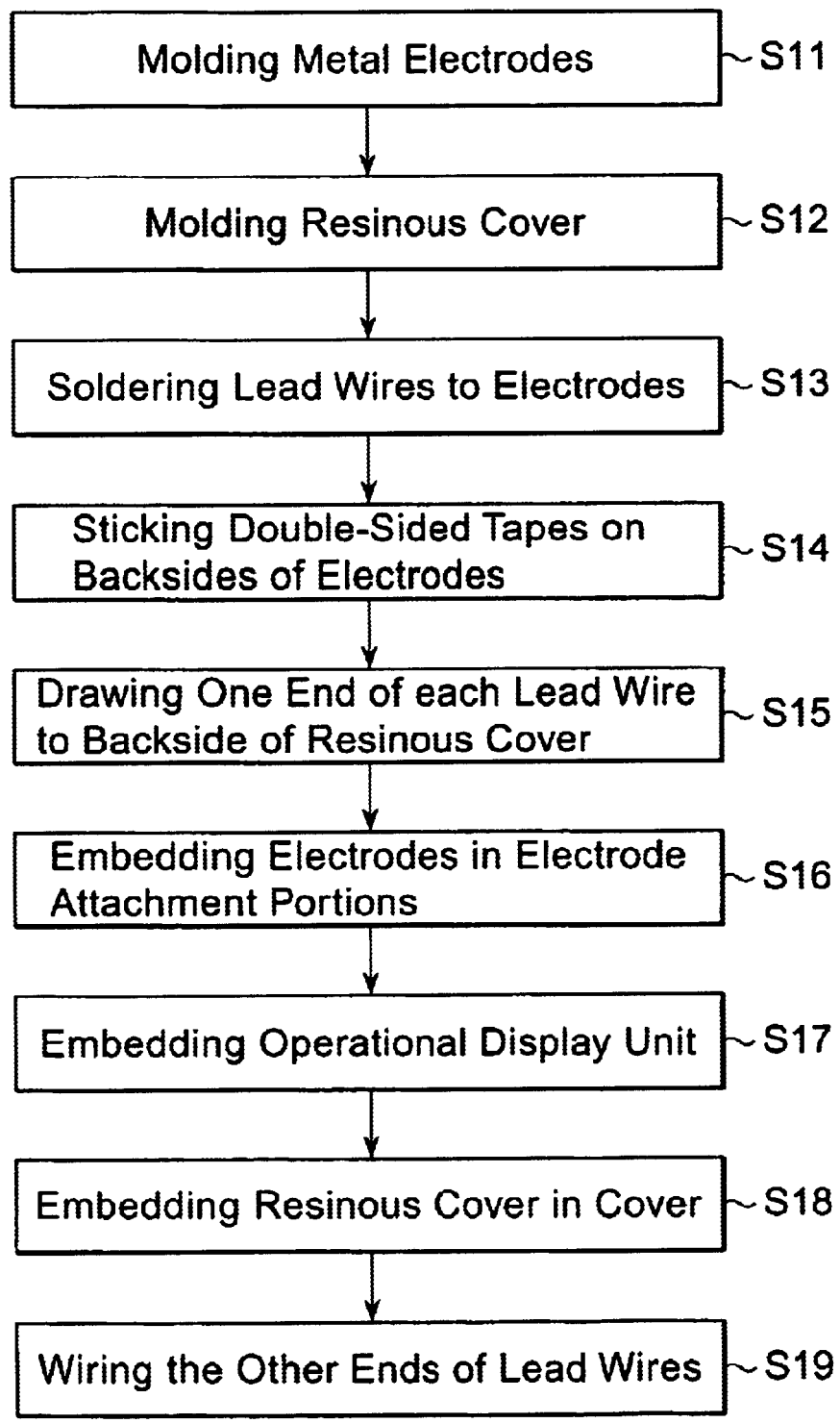
FIG. 8 is a flow chart showing manufacturing processes according to the prior art.

Comparing the manufacturing processes according to the present invention with those in the prior art, the processes of embedding the electrodes in the resinous cover which are conventionally required (steps S13 to S16 in FIG. 8), become unnecessary, since, in the present invention, the electrodes are integrally-molded together with the resinous cover. Further, since the embedding processes which conventionally need to be performed manually are unnecessary in the present invention., the processes in the present invention will greatly be decreased in number. Even a four-electrodes molding (step S11) can be done in a single process.

The distinction between the electrodes 5 to 8 and the insulating portion 9 should be made by coloring them different colors. Also, the distinction between these elements may be made by differentiating the respective degrees of smoothness of the surfaces thereof. For example, the surfaces of the electrodes are made rough, while that of the insulating portion is made smooth.

A second embodiment of the electrodes for use in the bioelectrical impedance measuring apparatus in accordance with the present invention, will now be explained. In the second embodiment, apparent shapes of the electrodes shown in the first embodiment can be designed with a wide degree of flexibility.

Figure 4:
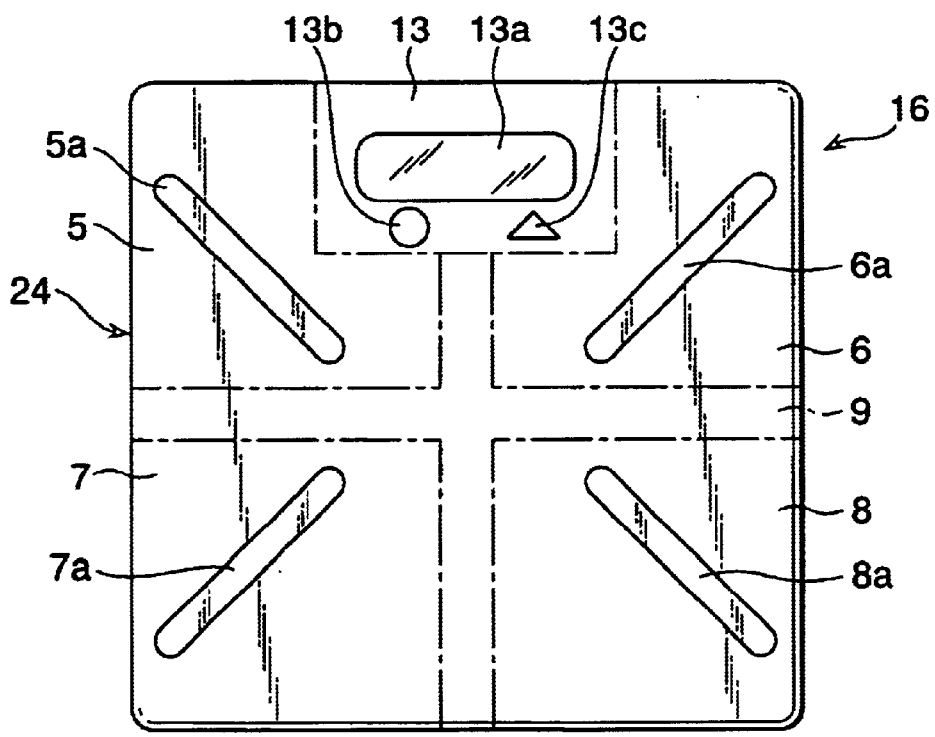
FIG. 4 is a top view of a resinous cover of a body fat meter for explaining a second embodiment according to the present invention.

FIG. 4 illustrates a top view of a resinous cover of a body fat meter of the second embodiment. The resinous cover 24 of the body fat meter 16 of the second embodiment is such that apparent electrodes 5a, 6a, 7a and 8a are added to the resinous cover 4 shown in FIG. 1, but the other elements thereof are the same as those in FIG. 1. For the electrode 5, the electrode 5a is an apparent electrode. The apparent electrodes 5a to 8a are formed within the area occupied by the electrodes 5 to 8, respectively. The electrodes 5, 6, 7 and 8 and the insulating portion 9 are colored the same color. The apparent electrodes 5a, 6a, 7a and 8a are colored a color different from that of the electrode 5.

Figure 5:
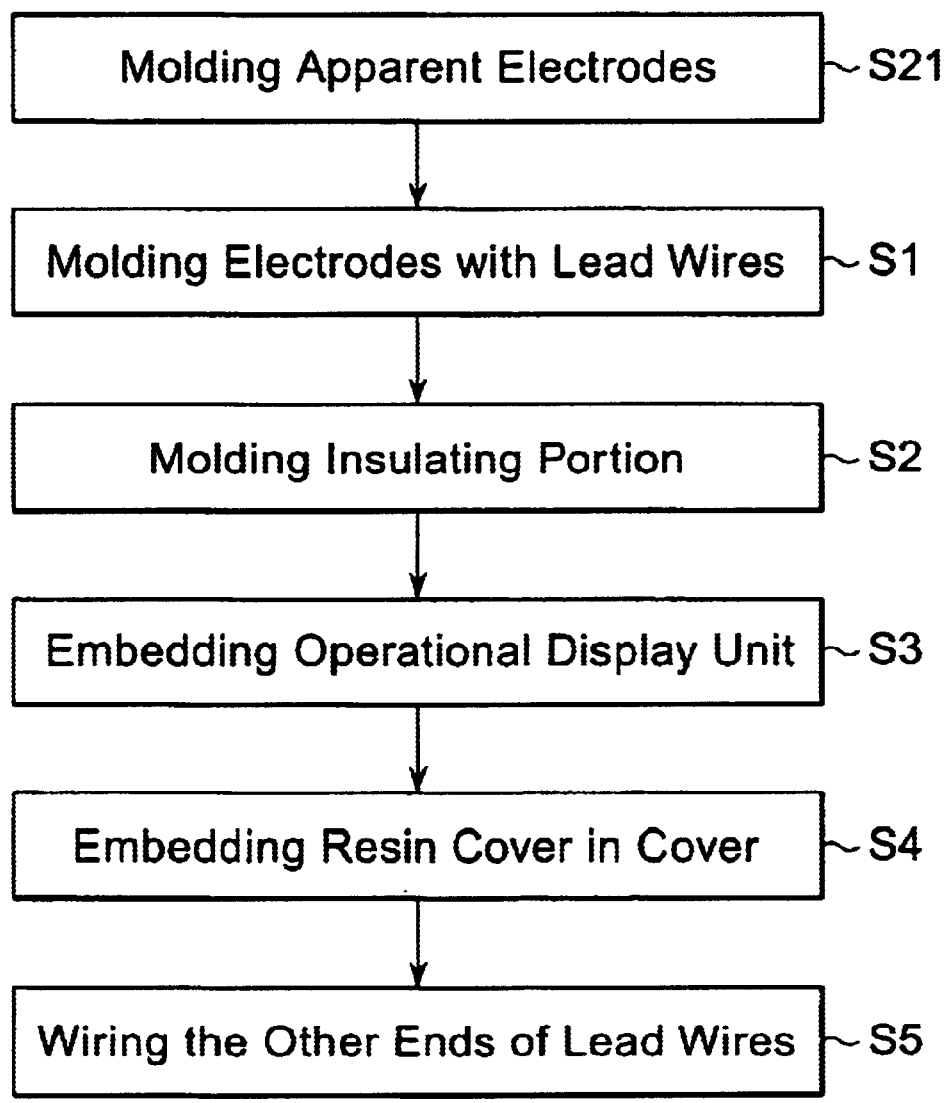
FIG. 5 is a flow chart showing manufacturing processes according to the second embodiment of the present invention.

With reference to a flow chart in FIG. 5, manufacturing processes of the resinous cover 24 according to the second embodiment will now be explained. The steps in FIG. 5 the same as those in FIG. 3 showing the manufacturing processes of the first embodiment are indicated by the same reference numbers as those in FIG. 3. As will be apparent from FIG. 5, only a first step S21 has been added to the steps in FIG. 3. In this step S21, apparent electrodes 5a, 6a, 7a and 8a are molded.

By way of an example, it is possible to freely change the apparent shape of the electrode within the area occupied by the electrode 5, so as to enhance the appearance thereof. It is difficult, due to a contact resistance between the electrodes and the living body to be measured, to make the apparent shape of the electrode shown in the present embodiment the same shape as the real shape of the electrode. However, in the electrodes of the present invention, since the area occupied by the electrodes is allowed to be wide, it is possible to freely design the apparent shapes of the electrodes, despite the contact resistance. The area of the electrode 5 can be made more than two times larger than that of the apparent electrode 5a.

In the above, although we have explained the body fat meter by giving an example of a technique for measuring bioelectrical impedance in which the resinous cover of the present invention is used, it is possible to apply the present invention to all types of machines for measuring bioelectrical impedance to measure the total body water or the like.

Since the electrodes of the bioelectrical impedance measuring apparatus are made from materials of conductive resin and integrally-molded with the resinous cover, there is no need to affix the electrodes to the resinous cover by means of the double-sided tapes, and it is possible to provide the body fat meter at a low cost due to the great reduction in the number of the manufacturing processes and the reduction in the number of components. Also, because of the integral molding technique, the areas of the electrodes are allowed to be wide and it is possible to freely design the shapes of the apparent electrodes. That is, when the color of the apparent electrode portions is differentiated from that of the resinous cover, it is possible to freely design the apparent shapes of the apparent electrodes and thus it is possible to enhance the appearance thereof. Further, since the electrodes are made from resin, they cause little the feet to feel cool when the feet are mounted thereon, and also it is possible to provide electrodes for the bioelectrical impedance measuring apparatus with a wide contact area and with high accuracy.

What is claimed is:

1. A resinous cover for use in a bioelectrical impedance measuring apparatus, comprising electrodes and an insulating portion comprising resin between the electrodes, wherein said electrodes and said insulating portion are integrally-molded, said electrodes and said insulating portion contact a skin of a body, the material of said electrodes is conductive resin, wherein the color of said electrodes and that of said insulating portion are different from each other.

2. The resinous cover in accordance with claim 1, wherein the degree of smoothness of the surfaces of said electrodes and that of said insulating portion are different from each other.

3. The resinous cover in accordance with claim 2, wherein the surface of either of said electrodes or said insulating portion is made rough and the surface of the other is made smooth.

4. The resinous cover in accordance with any one of claims 1, 4 or 5, wherein apparent electrodes are formed within the areas occupied by said electrodes.

5. The resinous cover in accordance with claim 4, wherein each of the areas of said electrodes is more than two times larger than that of its apparent electrode.

6. The resinous cover in accordance with claim 4, wherein the color of the areas occupied by said electrodes other than the areas occupied by said apparent electrodes and the color of said insulating portion are the same as each other.

7. A resinous cover in accordance with any one of claims 1, 2 or 3, wherein said bioelectrical impedance measuring apparatus is a body fat meter with a body weight meter.

8. The resinous cover in accordance with claim 1, wherein apparent electrodes are formed within the areas occupied by said electrodes.

9. The resinous cover in accordance with claim 8, wherein each of the areas of said electrodes is more than two times larger than that of its apparent electrode.

10. The resinous cover in accordance with claim 5, wherein the color of the areas occupied by said electrodes other than the areas occupied by said apparent electrodes and the color of said insulating portion are the same as each other.

11. A resinous cover in accordance with claim 1, wherein said bioelectrical impedance measuring apparatus is a body fat meter with body weight meter.

12. A resinous cover in accordance with claim 4, wherein said bioelectrical impedance measuring apparatus is a body fat meter with body weight meter.

13. A resinous cover in accordance with claim 8, wherein said bioelectrical impedance measuring apparatus is a body fat meter with body weight meter.

14. A resinous cover in accordance with claim 5, wherein said bioelectrical impedance measuring apparatus is a body fat meter with body weight meter.

15. A resinous cover in accordance with claim 9, wherein said bioelectrical impedance measuring apparatus is a body fat meter with body weight meter.

16. A resinous cover in accordance with claim 6, wherein said bioelectrical impedance measuring apparatus is a body fat meter with body weight meter.

17. A resinous cover in accordance with claim 10, wherein said bioelectrical impedance measuring apparatus is a body fat meter with body weight meter.

* * * * *

UNITED STATES PATENT AND TRADEMARK OFFICE
CERTIFICATE OF CORRECTION

PATENT NO.    : 6,738,660 B2                                          Page 1 of 1
DATED         : May 18, 2004
INVENTOR(S)   : Ikuo Hakomori et al.

It is certified that error appears in the above-identified patent and that said Letters Patent is hereby corrected as shown below:

<u>Column 4,</u>
Line 66, change "claims 1,4 or 5," to -- claims 1, 2 or 3, --

Signed and Sealed this

Fifth Day of October, 2004

JON W. DUDAS
*Director of the United States Patent and Trademark Office*